United States Patent
Köcher et al.

(10) Patent No.: US 7,317,112 B2
(45) Date of Patent: *Jan. 8, 2008

(54) CATALYSTS FOR SELECTIVE ISOCYANATE DIMERIZATION

(75) Inventors: Jürgen Köcher, Langenfeld (DE); Hans-Josef Laas, Bergisch Gladbach (DE)

(73) Assignee: Bayer MaterialScience AG, Leverkusen (DE)

( * ) Notice: Subject to any disclaimer, the term of this patent is extended or adjusted under 35 U.S.C. 154(b) by 356 days.

This patent is subject to a terminal disclaimer.

(21) Appl. No.: 10/910,982

(22) Filed: Aug. 4, 2004

(65) Prior Publication Data

US 2005/0033006 A1    Feb. 10, 2005

(30) Foreign Application Priority Data

Aug. 7, 2003    (DE) ................. 103 36 184

(51) Int. Cl.
*C07D 229/00*    (2006.01)

(52) U.S. Cl. ................. 548/951; 252/182.2; 540/202; 544/67; 544/68; 544/193; 544/222; 548/952; 528/51; 528/52; 528/53; 528/57; 528/73

(58) Field of Classification Search ............ 252/182.2; 540/202; 544/67, 68, 193, 222; 548/951, 548/952; 528/51, 52, 53, 57, 73
See application file for complete search history.

(56) References Cited

U.S. PATENT DOCUMENTS

| | | | |
|---|---|---|---|
| 3,829,525 A | 8/1974 | Cole et al. ............. 260/683.63 |
| 4,324,879 A | 4/1982 | Bock et al. .................. 528/45 |
| 4,379,905 A * | 4/1983 | Stemmler et al. .............. 528/73 |
| 4,476,054 A | 10/1984 | Disteldorf et al. .......... 260/239 |
| 4,912,210 A | 3/1990 | Disteldorf et al. .......... 540/202 |
| 4,960,848 A * | 10/1990 | Scholl et al. ................. 528/48 |
| 5,227,493 A | 7/1993 | Banks ........................ 546/307 |
| 7,060,817 B2 * | 6/2006 | Kocher et al. ............. 540/202 |
| 2003/0078450 A1 | 4/2003 | Kocher et al. ................ 560/26 |
| 2004/0014970 A1 | 1/2004 | Bernard ...................... 544/200 |

FOREIGN PATENT DOCUMENTS

| | | | |
|---|---|---|---|
| CA | 1335990 | * | 6/1995 |
| DE | 197 54 749 | | 7/1999 |
| GB | 1153815 | | 5/1969 |
| WO | 03/029217 A2 | | 4/2003 |

OTHER PUBLICATIONS

Database CA 'Online! Chemical Abstracts Service, Columbus, Ohio, US; 1962, Kostsova, A.G. et al: "Properties of .alpha.-aminopyridides of alkanesulfonic acids" XP002305422 gefunden im STN Database accession No. 58:33271 Zusammenfassung & Zhurnal Obshchei Khimii, 32, 1009-10 Coden: ZOKHA4; ISSN: 0044-460X, 1962.

J. Prakt. Chem., 336, (month unavailable) 1994, pp. 185-200, Hans Josef Laas et al, Zur Synthese aliphatischer Polyisocyanate—Lackpolyisocyanate mit Biuret-, Isocyanurat- oder Uretdionstruktur.

Die Angewandte Makromolekulare Chemie 141, (month unavailable) 1986, pp. 173-183, D. Wendisch et al, "Kernresonanzspektroskopische Beiträge zur Struktur und Stereochemie von (cyclo)aliphatischen Isocyanaten und deren Folgeprodukten".

* cited by examiner

*Primary Examiner*—John M. Cooney, Jr.
(74) *Attorney, Agent, or Firm*—Noland J. Cheung

(57) ABSTRACT

A method of dimerizing isocyanates using sulphonamide anions as a dimerization catalyst for the isocyanates and also to a process for preparing oligomeric isocyanates using such catalysts.

6 Claims, No Drawings

CATALYSTS FOR SELECTIVE ISOCYANATE DIMERIZATION

CROSS REFERENCE TO RELATED PATENT APPLICATION

The present patent application claims the right of priority under 35 U.S.C. § 119 (a)-(d) of German Patent Application No. 103 36 184.7, filed Aug. 7, 2003.

FIELD OF THE INVENTION

The present invention relates to the use of sulphonamide salts as dimerization catalysts for isocyanates and also to a process for preparing oligomeric isocyanates using the catalysts of the invention.

BACKGROUND OF THE INVENTION

Since monomeric diisocyanates cannot be used as crosslinkers in polyurethane coating systems, owing to their volatility and toxicological properties, the general approach is to use the higher molecular mass derivatives, examples being those on a uretdione, isocyanurate, biuret, urethane or allophanate basis. An overview of these polyisocyanates and how to prepare them is given for example in J. Prakt. Chem./Chem. Ztg. 1994, 336, 185-200. In the field of lightfast paints and coatings it is normal to use polyisocyanates based on aliphatic and/or cycloaliphatic diisocyanates.

The oligomerization (normally dimerization or triimerization) of isocyanates to form uretdiones, isocyanurates or iminooxadiazinediones is a long-known method well established in practice for the modification of generally difunctional $C_1$-$C_{30}$ isocyanates of low molecular mass. Specifically for isocyanate dimerization, however, there have to date been only a few usable catalysts which possess high activity and selectivity and are also suitable for use on the industrial scale.

An overview of the industrially relevant dimerization processes of the prior art and of the catalysts or catalyst systems they employ is given in J. Prak. Chem. 336 (1994) 185-200. A disadvantage of the catalysts reported therein is their in some cases inadequate catalytic activity and poor selectivity towards dimerization; consequently there is a need for new, improved systems for industrial use in particular.

EP-A 45 995 describes the use of special peralkylated aminophosphines as catalysts for selectively dimerizing isophorone diisocyanate (IPDI) (trimer content <2% by weight). A substantial drawback of these compounds, however, is their oxidation sensitivity to phosphoramides (e.g. hexamethylphosphoramide (HMPA)), which possess a high carcinogenic potential, which is prohibitive for broad industrial use.

EP-A 317 744 describes a process for preparing linear (cyclo)aliphatic uretdiones by catalysis with 4-dimethylaminopyridines, such as 4-dimethylaminopyridine (4-DMAP). This process too delivers linear IPDI uretdiones virtually free from isocyanurate groups.

The catalysts both of EP-A 45 995 and of EP-A 317 744 exhibit only moderate catalytic activity and are inactive towards isocyanates whose NCO groups are attached exclusively to secondary carbon atoms (e.g. 4,4'-diisocyanatodicyclohexylmethane).

An improved catalytic activity is displayed by the azolate anions described in WO 02/92658, with cycloaliphatic diisocyanates in particular being converted to dimeric uretdiones with a high selectivity.

It was an object of the present invention, therefore, to provide new catalysts for dimerization which in addition to high selectivity also display a markedly improved catalytic activity and can be used on the industrial scale.

SUMMARY OF THE INVENTION

The present invention is directed to a method of dimerizing isocyanates that includes reacting the isocyanates in the presence of sulphonamide salts according to formula (I)

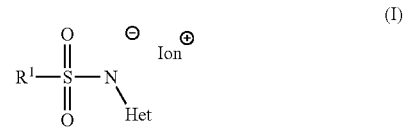

(I)

in which

R¹ is an aliphatic, cycloaliphatic, aromatic or araliphatic, optionally heteroatom-containing radical which is optionally substituted, Het is a radical selected from the group consisting of thiazolyl, benzthiazolyl, 2-pyrimidyl, 4-pyrimidyl, 2-pyridyl and 4-pyridyl and is optionally substituted and Ion$^{(+)}$ is an organic or inorganic cation.

The present invention is also directed to a method of preparing oligomeric isocyanates that includes reacting a) one or more organic compounds having an average NCO functionality ≧1 in the presence of b) a catalyst that includes one or more sulphonamide salts according to formula (I), and c) optionally solvents.

The present invention is further directed to polyisocyanate compositions obtained according to the above-described process as well as coatings, adhesive bonds or mouldings obtained from the polyisocyanate compositions and substrates coated with such coatings.

DETAILED DESCRIPTION OF THE INVENTION

Other than in the operating examples, or where otherwise indicated, all numbers or expressions referring to quantities of ingredients, reaction conditions, etc. used in the specification and claims are to be understood as modified in all instances by the term "about."

The object of the invention was achieved through the use of sulphonamide salts according to formula (I)

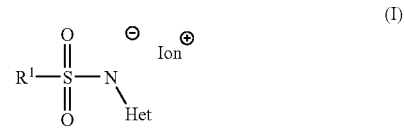

(I)

as catalysts for dimerizing isocyanates, in which

R¹ is an aliphatic, cycloaliphatic, aromatic or araliphatic, optionally heteroatom-containing radical which is optionally substituted, Het is a radical selected from the group consisting of thiazolyl, benzthiazolyl, 2-pyrimidyl, 4-pyrimidyl, 2-pyridyl and 4-pyridyl and is optionally substituted and Ion$^{(+)}$ is an organic or inorganic cation.

The invention accordingly provides for the use of sulphonamide anions of the general formula (I) for dimerizing isocyanates.

Preferred catalysts used are compounds of the general formula (II)

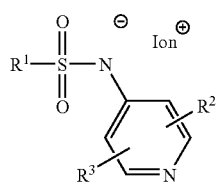

(II)

in which

R$^1$ is a saturated or unsaturated aliphatic or cycloaliphatic radical having up to 24 carbon atoms and optionally up to 3 heteroatoms from the group consisting of oxygen, sulphur and nitrogen, and is optionally substituted further, R$^2$ and R$^3$ independently of one another are identical or different groups selected from the group consisting of hydrogen, halogen, cyanide, nitro and dialkylamino and also optionally substituted alkyl, aryl, alkoxy and aryloxy radicals and Ion$^{(+)}$ is an alkali metal cation such as Li$^+$, Na$^+$ and K$^+$, for example, an alkaline earth metal cation such as Mg$^{2+}$ and Ca$^{2+}$, for example, or an ammonium or phosphonium ion of the general formula (III)

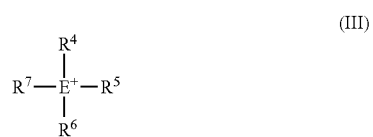

(III)

in which

E is nitrogen or phosphorus,

R$^4$, R$^5$ and R$^6$ independently of one another are hydrogen or identical or different saturated or unsaturated aliphatic or cycloaliphatic and optionally substituent-bearing radicals having up to 24 carbon atoms and optionally up to 3 heteroatoms from the group consisting of oxygen, sulphur and nitrogen, these radicals optionally being substituted by halogen atoms or hydroxyl groups, and R$^7$ corresponds to the definition of the radicals R$^4$, R$^5$ and R$^6$ or is a radical of the formula (IV)

(IV)

in which

X is a divalent, optionally substituted aliphatic, cycloaliphatic, araliphatic or aromatic C$_1$-C$_{12}$ radical and R$^4$, R$^5$, R$^6$ and E are as defined above.

Catalysts of the invention used with particular preference are compounds of the formula V

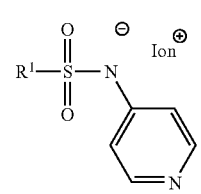

(V)

in which

R$^1$ is an aliphatic or cycloaliphatic C$_1$-C$_{18}$ radical optionally containing up to three heteroatoms from the group consisting of oxygen, sulphur and nitrogen and optionally containing substituents from the group consisting of halogen, nitro, cyanide, dialkylamino, alkyl, aryl, alkoxy and aryloxy, Ion$^{(+)}$ is an alkali metal cation or a monovalent ammonium or phosphonium cation of the general formula (IV) in which E is nitrogen or phosphorus and R$^4$, R$^5$, R$^6$ and R$^7$ independently of one another are a saturated aliphatic or cycloaliphatic or optionally substituted aromatic or araliphatic radical having up to 18 carbon atoms.

The invention further provides a process for preparing oligomeric isocyanates wherein a) one or more organic compounds having an average NCO functionality $\geq 1$ are oligomerized in the presence b) of a catalyst comprising one or more sulphonamide salts of the formula (I) and c) optionally solvents.

Into the process of the invention it is possible in component a) to insert all aliphatic, cycloaliphatic, araliphatic and/or aromatic isocyanates that are known to the person skilled in the art and have an average NCO functionality $\geq 1$, preferably $\geq 2$, individually or in any desired mixtures with one another, it being immaterial whether they have been prepared by phosgene or phosgene-free processes.

Preference is given to using aliphatic, cycloaliphatic and/or araliphatic isocyanates of the aforementioned kind, having a carbon skeleton (minus the NCO groups present) of 3 to 30, preferably 4 to 20, carbon atoms.

Particularly preferred compounds of component a) correspond to the aforementioned kind having aliphatically and/or cycloaliphatically attached NCO groups, such as, for example, bis(isocyanatoalkyl) ethers, bis- and tris-(isocyanatoalkyl)benzenes, -toluenes, and -xylenes, propane diisocyanates, butane diisocyanates, pentane diisocyanates, hexane diisocyanates (e.g. hexamethylene diisocyanate, HDI), heptane diisocyanates, octane diisocyanates, nonane diisocyanates (e.g. trimethyl-HDI (TMDI) generally as a mixture of the 2,4,4 and 2,2,4 isomers), nonane triisocyanates (e.g. 4-isocyanatomethyl-1,8-octane diisocyanate), decane diisocyanates, decane triisocyanates, undecane diisocyanates, undecane triisocyanates, dodecane diisocyanates, dodecane triisocyanates, 1,3- and 1,4-bis(isocyanatomethyl)cyclohexanes (H$_6$XDI), 3-isocyanatomethyl-3,5,5-trimethylcyclohexyl isocyanate (isophorone diisocyanate, IPDI), bis(4-isocyanatocyclohexyl)methane (H$_{12}$MDI), bis(isocyanatomethyl)norbornane (NBDI) or 3(4)-isocyanatomethyl-1-methylcyclohexyl isocyanate (IMCI).

Especially preferred compounds of component a) are hexamethylene diisocyanate (HDI), trimethyl-HDI (TMDI), 2-methylpentane 1,5-diisocyanate (MPDI), isophorone diisocyanate (IPDI), 1,3- and 1,4-bis(isocyanatomethyl)cyclohexane ($H_6$XDI), bis(isocyanatomethyl)norbornane (NBDI), 3(4)-isocyanatomethyl-1-methylcyclohexyl isocyanate (IMCI) and/or 2,4'- and/or 4,4'-bis(isocyanatocyclohexyl)methane ($H_{12}$MDI) or mixtures of these isocyanates.

The proportional use of monofunctional isocyanates is likewise possible where appropriate in particular cases.

In the process of the invention the amount of catalyst b) is from 0.01 to 10 mol %, preferably from 0.05 to 5 mol %, more preferably from 0.1 to 3 mol %, based on the amount of component a), the mol % figures here referring to the overall amount of substance, in mol, of the isocyanate of component a) employed. As catalyst b) of the process of the invention it is preferred to use exclusively sulphonamide salts of the formula (I).

Catalyst b) can be used undissolved, as the compound per se, or in the form of a solution in the process of the invention. In the latter case the solvent should be chosen such that, while dissolving the catalyst with molecular or ionic dissociation, it does not alter the composition and/or molecular structure of the sulphonamide anion(s) by chemical reactions. At the same time the solvent either must be inert towards NCO functions or may react with isocyanates only with the formation of urea, biuret, urethane or allophanate groups.

Where catalyst b) is used as a solution it is preferred to use straight-chain or branched alcohols having an average OH functionality$\geq$1 and 1 to 20, preferably 1 to 10, carbon atoms, such as, for example, methanol, ethanol, 1- and 2-propanol, the isomeric butanols, 2-ethylhexanol, 2-ethylhexane-1,3-diol, 1,3- and 1,4-butanediol or 1-methoxy-2-propanol.

In one preferred embodiment of the invention catalyst b) is used in the form of a solution.

In the process of the invention it is possible where appropriate to use solvents as component c) as well, though preference is given to using no further solvents as component c), besides the catalyst solvent optionally used.

The process of the invention is carried out preferably at temperatures from 0 to 100° C. or more preferably 20 to 100° C.

It will be appreciated that the process if necessary can also be carried out under increased or reduced pressure.

The process of the invention can be conducted either continuously or batchwise. A continuous process comprehends, for example, preparation in a tube reactor or by means of tank cascades, while batchwise processes are, for example, processes in one tank or one flask.

In one preferred embodiment of the invention the NCO oligomerization is taken to a conversion of 10-60 mol %, based on the total amount of NCO groups originally present, the oligomerization reaction is terminated, and unreacted isocyanate is separated off by means, for example, of distillation, optionally under reduced pressure, with the oligomerized isocyanate being obtained in the form of a resin.

Techniques suitable for terminating the oligomerization reaction include in principle all those known to the person skilled in the art (J. Prakt. Chem./Chem. Ztg. 1994, 336, 185-190). These include the removal of the catalyst by means, for example, of extraction or filtration, where appropriate with the assistance of an adsorptive carrier material, the inactivation of the catalyst system by thermal treatment and/or by adding acids or acid derivatives such as benzoyl chloride, phthaloyl chloride, phosphinous, phosphonous or phosphorous acid, phosphinic, phosphonic or phosphoric acid or the acidic esters of the abovementioned phosphorus acids. Preferred terminators are monoalkyl or dialkyl phosphates such as (di)butyl phosphate, (di)octyl phosphate or (di)trihexyl phosphate, sulphuric acid or its acidic esters, or sulphonic acids, such as preferably methanesulphonic acid and p-toluenesulphonic acid and alkyl esters of sulfonic acids, such as preferably p-toluenesulphonic acid methyl ester.

The amount of the catalyst poison required to terminate the reaction is guided by the amount of the active catalyst. Generally speaking, 50-150 mol % of terminator, based on the amount of catalyst originally employed, is used; preference is given to using equimolar amounts of terminator, based on the amount of catalyst employed.

The polyisocyanates obtained by the process of the invention can be isolated and purified by the customary methods of the state of the art, such as thin-film distillation, extraction, crystallization and/or molecular distillation, for example. They are obtained as colourless or only slightly coloured liquids or solids.

A particular advantage of the catalysts of the invention for isocyanate oligomerization is their high selectivity for the formation of uretdione structures; they are highly active in this context. In the case of the cycloaliphatic isocyanates in particular the catalysts of the invention additionally exhibit a propensity to form NCO dimers which is high for ionic catalysts.

The polyisocyanates prepared in accordance with the invention represent starting materials with diverse possible uses for the preparation of polymers, such as foamed or unfoamed plastics or polyurethane paints, for example, especially for preparing one- and two-component polyurethane paints, coatings, adhesives and adjuvants for application to materials such as wood, plastic, leather, metal, paper, concrete, masonry, ceramic and textile, for example.

EXAMPLES

The percentages for the conversion are calculated by dividing the amount of isocyanate converted by the total amount of isocyanate employed multiplied by 100. All other percentage figures are to be understood, unless noted otherwise, as percentages by weight.

Abbreviations used:
DMSO: dimethyl sulphoxide
i-PrOH: isopropanol
n-Bu: n-butyl-
Hex: n-hexyl- Colour numbers were measured in accordance with DIN standard 53995 (instrument: LICO 200, Dr. Lange GmbH, Berlin, DE).

The NCO content of the resins described in the inventive and comparative examples was determined by titration in accordance with DIN 53 185.

The dynamic viscosities of the polyisocyanate resins were determined at 23° C. using the viscometer VT 550, cone and plate measurement setup PK 100, from Haake (Karlsruhe, Germany). Measurements at different shear rates ensured that the rheology of the polyisocyanate mixtures of the invention described, like that of the comparison products, corresponds to that of ideal Newtonian liquids. It is therefore unnecessary to state the shear rate.

The crude products prepared were investigated by means of $^1$H-NMR spectroscopy on a DPX 400 from Bruker, Karlsruhe, Germany, at a $^1$H resonance frequency of 400 MHz. The reference used for the ppm scale was tetramethylsilane, as internal standard.

To determine the isocyanate conversion 20 to 40 mg of the reaction mixtures prepared were dissolved in 3 ml of chloroform and analyzed by gel permeation chromatography (column MZ-Gel Sdplus 500A 5 μm, MZ-Analysentechnik, Mainz, Germany). Owing to the high level of dilution of the measurement solution there was no need to deactivate the catalyst. The NCO conversion or resin yield can be calculated from the amount of monomeric isocyanate found.

Subsequent determination of the selectivity of the catalyst used was carried out by analyzing the possible structural types 1 to 3.

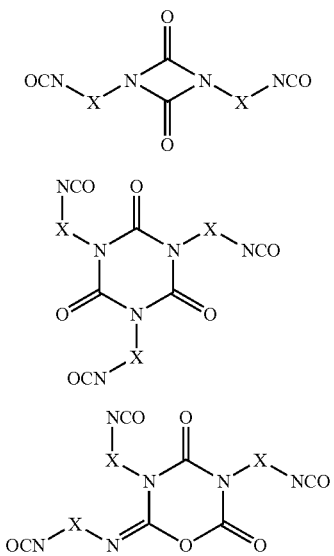

X=carbon skeleton

This was done by subjecting 30 μl of the reaction mixture to measurement between KBr plates by IR spectroscopy (spectrometer: Arid-Zone® from Bomem, Quebec, Canada, scan count 10, resolution 2 cm$^{-1}$). The vibrations at 1760 cm$^{-1}$ (structural type 1), 1690 cm$^{-1}$ (structural type 2) and 1780 cm$^{-1}$ (structural type 3) can be used to demonstrate the formation of structural types 1-3. Where more than one structural type alone was formed, $^{13}$C-NMR measurements were carried out for quantitative evaluation and the quantities of product were calculated by way of the signal integration.

For the $^{13}$C-NMR analysis 0.5 ml of each reaction mixture was admixed with stoichiometric amounts (based on the amounts of catalyst employed) of di-n-butyl phosphate in order to deactivate the catalyst and prevent further reaction. Deuterated chloroform was added to give a concentration of approximately 50% by weight resin. Measurements were made on a DPX 400 from Bruker, Karlsruhe, DE at a $^{13}$C resonance frequency of 100 MHz. The reference used for the ppm scale was tetramethylsilane, as internal standard. Data for the chemical shift of the compounds in question are taken from the literature (cf. Die Angewandte Makromolekulare Chemie 1986, 141, 173-183 and references cited therein) and/or obtained by subjecting model substances to measurement.

Catalyst Preparation

Example 1

Preparation of n-butyl-N-4-pyridylsulphonamide 51.0 g of 4-aminopyridine (0.542 mol) and 75.0 ml of triethylamine (54.8 g, 0.542 mol) were dissolved at 50° C. in 540 ml of THF. Again at 50° C., 70.3 ml of n-butanesulphonyl chloride (84.9 g, 0.542 mol) were added dropwise to this solution over the course of 1 h. After 19 h of stirring at 50° C. the reaction mixture was diluted with 500 ml of methylene chloride and extracted twice with 500 ml of 1 N NaOH. The aqueous phase was adjusted to a pH of 6-7 with concentrated HCl and then extracted with 500 ml of methylene chloride. The organic phase was dried over magnesium sulphate and the methylene chloride was removed by distillation. The 30 g of crude product obtained were recrystallized from acetonitrile. This gave 19.0 g of clean product. The constitution of the compound was verified by NMR-spectroscopy.

Example 2

Preparation of methyl-N-4-pyridylsulphonamide 9.9 g of 4-aminopyridine (104.8 mmol) and 14.5 ml of triethylamine (10.6 g, 104.8 mmol) were dissolved at room temperature in 72 ml of dimethylformamide. Likewise at room temperature, 8.1 ml of methanesulphonyl chloride (12.0 g, 104.8 mmol) were added dropwise to this solution over the course of one hour. The exothermic reaction meant that the temperature had to be maintained by ice bath cooling. After 20 h of stirring at room temperature the solvent was distilled off in vacuo. The residue which remained was taken up in 100 ml of methylene chloride and in 150 ml of 1 N NaOH. The organic phase was separated off. The aqueous phase was adjusted cautiously to a pH of 4 admixed with 100 ml of EtOH and 100 ml of methylene chloride. After the organic phase had been separated off, the aqueous phase was further admixed three times with 100 ml of EtOH and 100 ml of methylene chloride. The collected organic phases were freed from the solvent, and the crude product which remained was recrystallized from acetonitrile. This gave 3.2 g of product. The constitution of the compound was verified by NMR spectroscopy.

Example 3

Preparation of n-propyl-N-4-pyridylsulphonamide 47.6 g of 4-aminopyridine (0.506 mol) and 70.0 ml of triethylamine (51.1 g, 0.506 mol) were dissolved at 50° C. in 500 ml of THF. Likewise at 50° C., 57.3 ml of n-propanesulphonyl chloride (72.2 g, 0.506 mol) were added dropwise to this solution over the course of 1 h. After 19 h of stirring at 50° C. the reaction mixture was diluted with 500 ml of methylene chloride and extracted once with 500 ml of 1 N NaOH. The aqueous phase was adjusted to a pH of 5-6 with concentrated HCl, 100 ml of ethanol were added and then the mixture was extracted 5 times with 200 ml of methylene chloride. These organic phases were dried over magnesium sulphate and then the methylene chloride was removed by distillation. The 74 g of crude product obtained were recrystallized from acetonitrile. This gave 20.8 g of clean product. The constitution of the compound was verified by NMR spectroscopy.

Example 4

Preparation of the Sulphonamide Salts

A solution of 4.7 mmol of the sulphonamide in question in 8 ml of methanol was added dropwise at room temperature to 0.9 ml of a 30% strength Na methoxide solution in methanol (4.7 mmol), followed by stirring at room temperature for one hour. Subsequently 4.7 mmol of the ammonium salt or phosphonium salt were added and stirring was again continued at room temperature for one hour. The precipitated NaCl was then removed by filtration, the filtrate was freed from the solvent in vacuo, and the residue thus obtained was dried in vacuo.

For Example 4i a tenfold batch was implemented.

| Reactants | 4a | 4b | 4c | 4d | 4e | 4f | 4g | 4h | 4i |
|---|---|---|---|---|---|---|---|---|---|
| Sulphonamide from Example 1 | 1.0 g | 1.0 g | 1.0 g | 1.0 g | | | | | |
| Sulphonamide from Example 2 | | | | | 0.8 g | 0.8 g | 0.8 g | 0.8 g | |
| Sulphonamide from Example 3 | | | | | | | | | 10 g |
| [Bu$_4$N]Cl, 61.4% in isopropanol | 2.1 g | | | 2.1 g | | | | | |
| [Bu$_4$P]Cl, 71.4% in isopropanol | | 2.0 g | | | | 2.0 g | | | |
| [Bu$_3$P—C$_{14}$H$_{29}$]Cl | | | 2.1 g | | | | 2.1 g | | |
| [Hex$_3$P—C$_{14}$H$_{29}$]Cl | | | | 2.4 g | | | | 2.4 g | 27.9 g |

Examples 5 to 7

Inventive Oligomerization Reactions

General Instructions

The amounts of pure catalyst indicated in Tables 1-3 were weighed out into glass vessels with a septum seal. Each vessel was then evacuated twice and filled with argon. A syringe was used subsequently to add the indicated amounts of diisocyanate via the septum.

Where the catalyst was used as a solution (Examples 5b, c, d, e, 6i, 6j and 7h) the reaction vessel with septum seal was evacuated twice and filled with argon. A syringe was used to introduce 5 ml of each diisocyanate into the vessel thus prepared, after which the corresponding amounts of catalyst in the solvent stated were added with stirring.

The reaction mixture obtained was subsequently reacted under the conditions indicated in Tables 1 to 3 in an oil bath or in a stirred heating block (e.g. Variomag reaction block type 48.2/RM from H&P Labortechnik GmbH, Oberschleißheim, Germany).

Analysis was carried out as indicated above.

TABLE 1

Results of the inventive HDI oligomerization

| Ex. | Cat. | Amount [mol %] | Form used | Time [h] | T [° C.] | Conversion [%] | Type 1 [mol %] | Type 2 [mol %] |
|---|---|---|---|---|---|---|---|---|
| 5a | 4a | 0.05 | 100% | 0.08 | 40 | 33 | 27 | 73 |
| 5b | 4c | 0.08 | 0.1 M/DMSO | 3.5 | 40 | 26 | 49 | 51 |
| 5c | 4c | 0.1 | 0.1 M/DMSO | 3.5 | 40 | 38 | 42 | 58 |
| 5d | 4d | 0.25 | 1.8 M/i-PrOH | 2 | 40 | 45 | 75 | 25 |
| 5e | 4d | 0.3 | 1.8 M/i-PrOH | 2 | 40 | 45 | 77 | 23 |
| 5f | 4f | 0.4 | 100% | 0.25 | 40 | 31 | 88 | 12 |
| 5g | 4f | 0.5 | 100% | 0.25 | 40 | 48 | 89 | 11 |
| 5h | 4g | 0.4 | 100% | 0.25 | 40 | 26 | 90 | 10 |
| 5i | 4g | 0.5 | 100% | 0.25 | 40 | 33 | 91 | 9 |
| 5j | 4h | 0.4 | 100% | 0.25 | 40 | 38 | 86 | 14 |
| 5k | 4h | 0.5 | 100% | 0.25 | 40 | 43 | 87 | 13 |

TABLE 2

Results of the inventive IPDI oligomerization

| Ex. | Cat. | Amount [mol %] | Form used | Time [h] | T [° C.] | Conversion [%] | Type 1 [mol %] | Type 2 [mol %] |
|---|---|---|---|---|---|---|---|---|
| 6a | 4a | 0.1 | 100% | 0.75 | 40 | 34 | 100 | 0 |
| 6b | 4a | 0.15 | 100% | 0.75 | 40 | 40 | 100 | 0 |
| 6c | 4b | 0.1 | 100% | 2 | 40 | 36 | 100 | 0 |
| 6d | 4b | 0.15 | 100% | 2 | 40 | 46 | 100 | 0 |
| 6e | 4c | 0.25 | 100% | 1 | 40 | 33 | 100 | 0 |
| 6f | 4c | 0.5 | 100% | 1 | 40 | 47 | 100 | 0 |
| 6g | 4d | 0.25 | 100% | 0.5 | 40 | 37 | 100 | 0 |
| 6h | 4d | 0.50 | 100% | 0.5 | 40 | 42 | 100 | 0 |
| 6i | 4d | 0.3 | 1.8 M/i-PrOH | 1.5 | 40 | 45 | 100 | 0 |
| 6j | 4d | 0.4 | 1.8 M/i-PrOH | 1.5 | 40 | 45 | 100 | 0 |
| 6k | 4f | 0.25 | 100% | 1 | 40 | 30 | 100 | 0 |

TABLE 2-continued

Results of the inventive IPDI oligomerization

| Ex. | Cat. | Amount [mol %] | Form used | Time [h] | T [° C.] | Conversion [%] | Type 1 [mol %] | Type 2 [mol %] |
|---|---|---|---|---|---|---|---|---|
| 6l | 4f | 0.5 | 100% | 1 | 40 | 36 | 100 | 0 |
| 6m | 4g | 0.25 | 100% | 1 | 40 | 33 | 100 | 0 |
| 6n | 4g | 0.5 | 100% | 1 | 40 | 42 | 100 | 0 |
| 6p | 4h | 0.25 | 100% | 1 | 40 | 33 | 100 | 0 |
| 6q | 4h | 0.5 | 100% | 1 | 40 | 48 | 100 | 0 |

TABLE 3

Results of the inventive $H_{12}$MDI oligomerization

| Ex. | Cat. | Amount [mol %] | Form used | Time [h] | T [° C.] | Conversion[%] | Type 1 [mol %] | Type 2 [mol %] |
|---|---|---|---|---|---|---|---|---|
| 7a | 4a | 0.75 | 100% | 1 | 40 | 25 | 20 | 80 |
| 7b | 4a | 1 | 100% | 1 | 40 | 31 | 17 | 83 |
| 7c | 4b | 0.25 | 100% | 23.5 | 40 | 42 | 100 | 0 |
| 7d | 4b | 0.5 | 100% | 23.5 | 40 | 44 | 100 | 0 |
| 7e | 4c | 0.5 | 100% | 4 | 40 | 32 | 100 | 0 |
| 7f | 4c | 1.0 | 100% | 4 | 40 | 37 | 100 | 0 |
| 7g | 4d | 1.0 | 100% | 21 | 40 | 40 | 100 | 0 |
| 7h | 4d | 1.5 | 1.8 M/i-PrOH | 42 | 40 | 24 | 100 | 0 |
| 7i | 4f | 1 | 100% | 23 | 40 | 25 | 100 | 0 |
| 7j | 4g | 0.75 | 100% | 21 | 40 | 24 | 100 | 0 |
| 7k | 4h | 1 | 100% | 16 | 40 | 21 | 100 | 0 |

Comparative Examples 1 to 3

The reaction of HDI, IPDI and $H_{12}$-MDI was carried out in accordance with the general instructions described above, using the following literature catalysts:

benzyltrimethylammonium hydroxide, cf. EP-A 0 010 589 (substance used is the product sold under the trade name Triton® B as a 40% strength methanolic solution by Aldrich), tri-n-butylphosphine, cf. DE-A 16 70 720 (catalyst: Cytop® 340, Cytec, undiluted), and 4-dimethylaminopyridine, cf. DE-A 37 39 549 (catalyst: 4-DMAP, Aldrich, undiluted)

The relevant results obtained using these non-inventive catalysts are set out in the tables below.

TABLE 4

Comparative Examples 1 a) and b): Reactions of HDI

| No. | Catalyst | Cat. conc. [mol %] | Time [h] | Temp. [° C.] | Conversion [%] | Type 1 [mol %] | Type 2 [mol %] | Type 3 [mol %] |
|---|---|---|---|---|---|---|---|---|
| 1a | Triton® B | 0.035 | 0.25 | 60 | 42.7 | 2.1 | 94.4 | 3.5 |
| 1b | n-Bu$_3$P | 1.30 | 1.5 | 60 | 40.6 | 69.7 | 15.7 | 14.6 |

TABLE 5

Comparative Examples 2 a)–f): Reactions of IPDI

| No. | Catalyst | Cat. conc. [mol %] | Time [h] | Temp. [° C.] | Conversion [%] | Type 1 [mol %] | Type 2 [mol %] |
|---|---|---|---|---|---|---|---|
| 2a | Triton® B | 0.07 | 2.5 | 60 | 43.1 | 2.1 | 97.9 |
| 2b | 4-DMAP | 1.7 | 24 | 40 | 30 | 98.8 | 1.2 |
| 2c | n-Bu$_3$P | 2 | 5.5 | 40 | 18.7 | 69.3 | 30.7 |

TABLE 6

Comparative Examples 3 a)–c): Reactions of $H_{12}MDI$

| No. | Catalyst | Cat. conc. [mol %] | Time [h] | Temp. [° C.] | Conversion [%] | Type 1 [mol %] | Type 2 [mol %] |
|---|---|---|---|---|---|---|---|
| 3a | Triton ® B | 0.2 | 21.5 | 40 | 51.7 | 1.2 | 98.8 |
| 3b | 4-DMAP | 2 | 456 | 40 | 14.3 | 97.8 | 2.2 |
| 3c | n-Bu$_3$P | 2 | 48 | 40 | 3.9 | 86.5 | 13.5 |

As can be seen, the tetraalkylammonium hydroxide of saltlike construction is highly active but yields only low uretdione fractions in the product mixture. The two covalently constructed catalysts do yield high uretdione fractions in the product mixture, but their activity is low, so that even when high catalyst concentrations are employed, particularly in the case of the cycloaliphatic diisocyanates IPDI and $H_{12}$MDI, conversion is very slow.

In contrast to the catalysts of the comparative experiments the catalysts of the invention are very selective dimerization catalysts with a higher activity, as shown by comparing the results relating to the reaction of IPDI. For $H_{12}$MDI, the comparative experiment catalysts 4-dimethylaminopyridine and tri-n-butylamine are indeed selective for the dimerization, but with a very low activity. The catalysts of the invention have distinct advantages here in the high activity in association with equally high or even higher selectivity for the dimerization.

Example 8

Process Examples

A) Inventive 1000 g (4.50 mol) of isophorone diisocyanate (IPDI) were introduced into a vessel at 30° C. and with dry nitrogen. With stirring, 15 g (0.022 mol) of the catalyst of Example 4i were then added continuously by means of a laboratory infusion pump (KDS 100, KD Scientific, Boston, USA) over a reaction time of 3 hours. Under these conditions the oligomerization reaction ran with no discernible exotherm. After the end of catalyst addition the reaction mixture was stirred for 10 minutes and thereafter the catalyst was deactivated by addition of 5 g (0.024 mol) of dibutyl phosphate. A clear, colourless reaction mixture was obtained which had an NCO content of 28.5%, corresponding to a degree of oligomerization of 24.6%. The reaction mixture was subsequently freed from excess diisocyanate by means of a thin-film evaporator at a temperature of 160° C. and a pressure of 0.3 mbar. In this way a virtually colourless uretdione polyisocyanate was obtained which had a free NCO content of 17.5%, a monomeric IPDI content of 0.4%, a viscosity of more than 200 000 mPas (23° C.) and a colour number (APHA), determined on a 10% strength solution in methylene chloride, of 12. According to $^{13}$C-NMR and IR spectroscopy the product contained uretdione groups exclusively. Isocyanurate structures were not detectable.

B) Comparative (in accordance with EP-A 317 744)

1000 g (4.50 mol) of isophorone diisocyanate (IPDI) were admixed at room temperature with 20 g (0.164 mol) of 4-dimethylaminopyridine (DMAP) as catalyst, under dry nitrogen and with stirring. After 20 h the pale yellow reaction mixture, which had an NCO content of 28.7%, corresponding to a degree of oligomerization of 22.6%, was freed from volatile constituents without the addition of a catalyst poison beforehand, using a thin-film evaporator at a temperature of 160° C. and a pressure of 0.3 mbar. This gave a pale yellow uretdione polyisocyanate of high viscosity which had a free NCO group content of 17.6%, a monomeric IPDI content of 0.4% and a colour number (APHA), determined on a 10% strength solution in methylene chloride, of 62. According to its $^{13}$C-NMR and IR spectra the product was free from isocyanurate structures.

The comparison demonstrates the higher activity of the catalyst of the invention as compared with catalysts according to EP-A 317 744. Despite a considerably lower catalyst concentration, pure (linear) uretdione polyisocyanates of IPDI can be prepared within a much shorter time, and in addition they have a distinctly improved colour.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of dimerizing isocyanates comprising reacting the isocyanates in the presence of sulphonamide salts according to the formula (I)

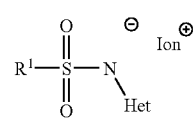

(I)

in which

R$^1$ is an aliphatic, cycloaliphatic, aromatic or araliphatic, optionally heteroatom-containing radical which is optionally substituted, Het is a radical selected from the group consisting of thiazolyl, benzthiazolyl, 2-pyrimidyl, 4-pyrimidyl, 2-pyridyl and 4-pyridyl and is optionally substituted and Ion$^{(+)}$ is an organic or inorganic cation.

2. The method according to claim 1, wherein

R$^1$ is an aliphatic or cycloaliphatic C$_1$-C$_{18}$ radical optionally containing up to three heteroatoms from the group consisting of oxygen, sulphur and nitrogen and optionally containing substituents from the group consisting of halogen, nitro, cyanide, dialkylamino, alkyl, aryl, alkoxy and aryloxy, Het is 4-pyridyl and Ion$^{(+)}$ is an alkali metal cation or a monovalent ammonium or phosphonium cation of the general formula (III)

(III)

in which

E is nitrogen or phosphorus, $R^4$, $R^5$ and $R^6$ independently of one another are hydrogen or identical or different saturated or unsaturated aliphatic or cycloaliphatic and optionally substituent-bearing radicals having up to 24 carbon atoms and optionally up to 3 heteroatoms from the group consisting of oxygen, sulphur and nitrogen, these radicals optionally being substituted by halogen atoms or hydroxyl groups, and $R^7$ corresponds to the definition of the radicals $R^4$, $R^5$ and $R^6$ or is a radical of the formula (IV)

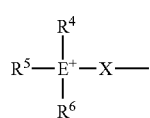

(IV)

in which

X is a divalent, optionally substituted aliphatic, cycloaliphatic, araliphatic or aromatic $C_1$-$C_{12}$ radical and $R^4$, $R^5$, $R^6$ and E are as defined above.

3. A method of preparing oligomeric isocyanates comprising reacting a) one or more organic compounds having an average NCO functionality $\geq$ 1 in the presence b) of a catalyst comprising one or more sulphonamide salts, and c) optionally solvents;

wherein the sulphonamide salts conform to figure (I):

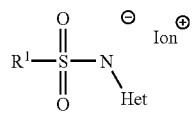

(I)

wherein $R^1$ is an aliphatic, cycloaliphatic, aromatic or araliphatic, optionally heteroatom-containing radical which is optionally substituted, Het is a radical selected from the group consisting of thiazolyl, benzthiazolyl, 2-pyrimidyl, 4-pyrimidyl, 2-pyridyl and 4-pyridyl and is optionally substituted and $Ion^{(+)}$ is an organic or inorganic cation.

4. The method according to claim 3, wherein the NCO oligomerization is carried out at a temperature of 20-100° C. until 10-60 mol % of all the NCO groups have undergone conversion and then the dimerization reaction is terminated by addition of a catalyst poison and unreacted monomeric isocyanate is separated off by distillation.

5. The method according to claim 3, wherein $R^1$ is an aliphatic or cycloaliphatic $C_1$-$C_{18}$ radical optionally containing up to three heteroatoms from the group consisting of oxygen, sulphur and nitrogen and optionally containing substituents from the group consisting of halogen, nitro, cyanide, dialkylamino, alkyl, aryl, alkoxy and aryloxy, Het is 4-pyridyl and $Ion^{(+)}$ is an alkali metal cation or a monovalent ammonium or phosphonium cation of the general formula (III)

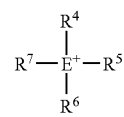

(III)

in which

E is nitrogen or phosphorus, $R^4$, $R^5$ and $R^6$ independently of one another are hydrogen or identical or different saturated or unsaturated aliphatic or cycloaliphatic and optionally substituent-bearing radicals having up to 24 carbon atoms and optionally up to 3 heteroatoms from the group consisting of oxygen, sulphur and nitrogen, these radicals optionally being substituted by halogen atoms or hydroxyl groups, and $R^7$ corresponds to the definition of the radicals $R^4$, $R^5$ and $R^6$ or is a radical of the formula (IV)

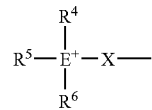

(IV)

in which

X is a divalent, optionally substituted aliphatic, cycloaliphatic, araliphatic or aromatic $C_1$-$C_{12}$ radical and $R^4$, $R^5$, $R^6$ and E are as defined above.

6. The method according to claim 2, wherein a) the isocyanates comprise one or more organic compounds having an average NCO functionality $\geq$ 1 and are dimerized in the presence b) of a catalyst comprising one or more sulphonamide salts according to formula (I), and c) optionally solvents.

* * * * *